United States Patent [19]
Shetty

[11] Patent Number: 5,906,941
[45] Date of Patent: May 25, 1999

[54] PLANT PROPAGATION COMPOSITIONS AND METHODS

[75] Inventor: Kalidas Shetty, Amherst, Mass.

[73] Assignee: University of Massachusetts, Boston, Mass.

[21] Appl. No.: 08/842,560

[22] Filed: Apr. 15, 1997

[51] Int. Cl.$^6$ .............................. C12N 5/04; A61K 35/12
[52] U.S. Cl. ......................... 435/431; 435/410; 504/118; 424/520
[58] Field of Search ..................... 435/40, 431; 504/118; 424/520

[56] References Cited

U.S. PATENT DOCUMENTS 4,960,703  10/1990  Paques et al. ........................... 435/410

OTHER PUBLICATIONS

Armstrong & Green, "Establishment and Maintenance of Friable, Embryogenic Maize Callus and the Involvement of L–Proline," Planta, 164:207–214, 1985.
Böttcher et al., "Induction and Reversion of Vitrification of Plants Cultured in vitro," Physiol. Plant., 72:560–564, 1988.
Chandler and Dodds, "The Effect of Phosphate, Nitrogen and Sucrose on the Production of Phenolics and Solasodine in Callus Cultures of Solanum Laciniatum," Plant Cell Rep., 2:105–108, 1983.
Debergh et al., "Mass Propagation of Globe Artichoke (Cynara scolymus): Evaluation of Different Hypotheses to Overcome Vitrification with Special Reference to Water Potential," Physiol. Plant., 53:181–187, 1981.
Endress, Plant Cell Biotechnology, pp. 33–34, 38, 116, Springer–Verlag, Berlin, 1994.
Gamborg et al., "Nutrient Requirements of Suspension Cultures of Soybean Root Cells," Exp. Cell Res., 50:151–158, 1968.
Kevers et al., "Physiological and Biochemical Events Leading to Vitrification of Plants Cultured in vitro," Physiol. Plant., 61:69–74, 1984.
Mackie, "Fish Protein Hydroysates," Process Biochem., 17:26–31, 1982.
Murashige, "Plant Propagation by Tissue Culture: A Practice with Unrealized Potential," in: Handbook of Plant Cell Culture, vol. 5, pp. 3–9, McGraw–Hill, New York, 1990.
Murashige & Skoog, "A Revised Medium for Rapid Growth and Bio Assays with Tobacco Tissue Cultures," Physiol. Plant. 15:473–497, 1962.
Roberts et al., Methods in Molecular Biology, vol. 6, Plant Cell and Tissue Culture, Pollard & Walker, eds. p. 234, The Humana Press, Clifton, N.J. 1990.
Ronchi et al., "Stimulation of Carrot Somatic Embryogenesis by Proline and Serine," Plant Cell Reports, 3:210–214, 1984.
Sato et al., "Recovering Vitrified Carnation (*Dianthus caryophyllus*L. ) Shoots using Bacto–Peptone and its Subfractions," Plant Cell Rep., 12:370–374, 1993.
Schenk & Hildebrandt, "Medium and Techniques for Induction and Growth of Monocotyledonous and Dicotyledonous Plant Cell Cultures," Can. J. Bot., 50:199–204, 1972.
Shetty at al., "Stimulation of Benzyladenine–Induced in vitro Shoot Organogenesis from Cotyledons of *Cucumis sativus*L. by Proline and Abscisic Acid," Plant Tissue Culture Letters, 9:104–108, 1992.
Shetty et al., "Stimulation of Benzyladenine–Induced in vitro Shoot Organogenesis in *Cucumis melo*L. by Proline, Salicylic Acid and Aspirin," Plant Sci., 84:193–199, 1992.
Shetty et al., "Prevention of Vitrification Associated with in vitro Shoot Culture of Oregano (*Origanum vulgare*) by Pseudomonas spp.," J. Plant Physiol., 147:447–451, 1995.
Shetty & Asano, "Specific Selection of Embryogenic Cell Lines in *Agrostis Alba*L. using the Proline Analog Thioproline," Plant Science, 79:259–263, 1991.
Shetty & McKersie, "Proline, thioproline and potassium mediated stiumulation of somatic embryogenesis in alfalfa (*Medicago saiva*L. ),"Plant Sci., 88:185–193, 1993.
Stuart & Strickland, "Somatic Embryogenesis from Cell Cultures of *Medicago sativa*L. I. The role of Amino Acid Additions to the Regeneration Medium," Plant Sci. Letters 34:165–174, 1984.
Stuart & Strickland, "Somatic Embryogenesis from Cell Cultures of *Medicago sativa*L. II. The Interaction of of Amino Acids with Ammonium," Plant Sci. Letters, 34:175–181, 1984.
Tarky et al., "Protein Hydrolysate from Fish Waste," J. Food Sci., 38:917–918, 1973.
Trigiano & Conger, "Regulation of Growth and Somatic Embryogenesis by Proline and Serine in Suspension Cultures of *Dactylis glomerata*," J. Plant Physiol., 130: 49–55, 1987.
White, A Handbook of Plant Tissue Culture, p. 103, Jaques Cattell Press, Lancaster, Pennsylvania, 1943.

*Primary Examiner*—Leon B. Lankford, Jr.
*Attorney, Agent, or Firm*—Fish & Richardson P.C.

[57] ABSTRACT

The present invention relates to the discovery that fishery by-products, in particular fish protein hydrolysate, can be used as a source of nutrients in plant tissue culture. A composition can be made by mixing a plant tissue culture medium, a fishery by-product, and a buffer compound. The composition is used for culturing plant tissues, to promote somatic embryogenesis, reduce vitrification (hyperhydricity) in cultured tissues, and to enhance acclimation of plants by both reducing the amount of time required for acclimation, and by increasing the survival rate of plants through the acclimation process.

24 Claims, No Drawings

PLANT PROPAGATION COMPOSITIONS AND METHODS

BACKGROUND OF THE INVENTION

The invention relates to new compositions and methods of plant tissue culture.

Plant tissue culture is the growth, on or in artificial media, of whole plants, plants parts, organs, or undifferentiated tissue. Tissue culture has many important commercial uses such as the isolation and maintenance of virus-free strains of plants. Plant tissue culture can also be used to mass-propagate plants, and this method is used routinely in the propagation of horticultural and floral varieties for the nursery industry.

Certain difficulties detract from the benefits of tissue culture. For example, certain cultured plant tissues, in any stage of development, may be subject to vitrification (also called hyperhydricity), which results in enlarged, thick, translucent, and brittle malformations of tissue. These malformations are irreversible, and affected tissues typically degenerate and die.

Acclimation is another common problem in tissue culture. Once whole plantlets are successfully generated, they must be acclimated before being transplanted. Plants normally grow a waxy outer cuticle to prevent evaporative water loss, but the high humidity of the tissue culture environment prevents development of this protective coating. A sudden drop in humidity, such as transfer into a growth chamber or greenhouse, can kill the young plants.

A third problem is that the chemical composition of the culture medium has a large effect on all of these phenomena. Each cell, tissue source, organ type, and developmental pathway has different nutritional requirements, and these can vary greatly between species, or even between cultivars within a given specie. Determining the ideal medium for a new plant or tissue must be done through systematic trial-and-error, using knowledge of the behavior of related species as a starting point (Endress, 1994, *Plant Cell Biotechnology*, Springer-Verlag, Berlin, pgs. 38).

SUMMARY OF THE INVENTION

The invention is based on the discovery that fishery by-products, such as soluble fish protein hydrolysate (SFPH), can be used as a source of nutrients in plant tissue culture. SFPH can be used to enhance somatic embryo formation, leading to an increase in the efficiency of plant micropropagation. Inclusion of SFPH in the culture medium also controls vitrification, and aids in acclimation of the regenerated plantlets to the atmosphere outside of the tissue culture environment, resulting in higher survival rates.

In general, the invention features a method of using fishery by-products in plant tissue culture media for controlling vitrification of the cultured tissues, for enhancing the rate of somatic embryogenesis, and in aiding acclimation of regenerated plantlets to the ambient environment outside of culture.

In one embodiment, the invention features a composition for use in culturing plant tissues. The composition consists of a plant tissue culture medium, e.g., Murashige & Skoog medium, Schenk & Hildebrandt medium, White's medium, and Gamborg's B5 medium, and a fishery by-product, e.g., fish protein hydrolysate, unhydrolysed fish waste, fish meal, fish gurry, and fish offal, which are mixed in proportions to form a homogeneous mixture. The composition can be solid or liquid. The composition can also include compounds (e.g., acidic or basic compounds such as hydrochloric acid, acetic acid, or sodium hydroxide, to obtain a pH suitable to support the culture of plant tissues, e.g., 4.5 to 8.5, or 5.0 to 6.0), plant growth regulators, or amino acids, e.g., proline, and their analogs.

The fishery by-products are added in an amount adequate to increase production of somatic embryos by cultured plant tissues relative to use of the plant tissue culture medium without the fishery by-product, e.g., enough to increase the percentage of tissue explants which produce somatic embryos, or to increase the average number of embryos produced per explant, or both. The fishery by-products can also be added in an amount adequate to inhibit vitrification of cultured plant tissues relative to use of the plant tissue culture medium without the fishery by-product, e.g., enough to increase the amount of chlorophyll in the cultured tissues, to reduce the water content of the tissues, or both. The fishery by-products can be added in an amount adequate to improve acclimation of cultured plant tissues relative to use of the plant tissue culture medium without the added fishery by-product, e.g., enough to reduce the amount of time that the plantlets must be kept in closed containers, or to increase the percentage of plants that survive after removal from the closed containers, or both.

In another aspect, the invention features a method of using the new fishery by-product composition in plant tissue culture. The method includes obtaining the new composition and using it as a substrate for culturing plant tissues. The method can use the composition in solid or liquid form, and the pH of the composition can be adjusted through the addition of acidic or basic compounds. For example, the new method can be used to increase the rate of growth of plant tissues relative to a method using the tissue culture medium without the added fishery by-product.

"Fishery by-products" are any waste produced during fish processing. These can be treated or untreated wastes, and can be, for example, fish protein hydrolysate, unhydrolysed waste, fish meal, bones and offal, or gurry.

"Tissue culture medium" is a composition used as a nutrient source or substrate for growing, maintaining, and generating whole plants, plant parts, organs, cells, and undifferentiated tissue, and may contain chemicals, ground tissues, or extracts of biological origin, mixed in proportions dictated by well-known recipes (e.g., Schenk & Hildebrandt's, Murashige & Skoog's, White's, Nitsch's medium), or other formulations.

"Micropropagation" describes the creation of plants by methods of plant tissue culture.

"Somatic embryogenesis" is the production of plant embryos from cultured plant tissue, where each embryo has the potential to grow into a whole plant.

"Acclimation," or acclimatization, describes a process by which plants and plant tissues which were previously maintained in tissue culture, e.g., in closed containers, are adapted to the environment outside of tissue culture, e.g., a growth chamber, a greenhouse, or the out-of-doors.

A "plant growth regulator" is a compound that acts on plant cells and causes a response in the growth of those cells. Depending on the compound, the response can be increased or decreased growth or abscission of plant parts, or the development of particular organs or tissues, e.g., roots, shoots, or flowers. Such compounds may be naturally occurring in plants (e.g., auxins, cytokinins, abscisic acid or ethylene), fungi (e.g., gibberellins), or the compounds may be synthetic, such as 2,4-dichlorophenoxyacetic acid (2,4-D), 2,4,5-trichlorophenoxyacetic acid (2,4,5-T, or Agent Orange), kinetin, 6-benzyl-aminopurine, zeatin, or isopentyl-γ,γ-dimethyl-allyl (2iP).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the suitable methods and materials are described below. All publications, patent applications, patents and other references mentioned herein are incorporated by reference in their entirety. In case of conflict, the present specification, including definitions, will control. In addition, the materials, methods, and examples are illustrative only and not intended to be limiting.

Advantages of the invention include the fact that it makes use of an industrial waste which is currently difficult to dispose of, and that this waste can be used to improve the efficiency with which plants are generated by tissue culture techniques. An additional advantage is that the fishery waste can be used as a complex nutritional ingredient in the culture of plants which cannot currently be grown in vitro because their nutritional needs are not yet fully understood.

Other features and advantages of the invention will be apparent from the following detailed description, and from the claims.

DETAILED DESCRIPTION

The invention is based on the discovery that fishery by-products such as SFPH can serve as a nutritional component in plant tissue culture media. For example, SFPH increases the number of somatic embryos generated by the cultured tissue, thereby enhancing the efficiency of micropropagation. SFPH also reduces vitrification of plant tissues during culture, and improves the acclimation of plants generated in tissue culture to the outside environment, thereby improving the survival rate of the clonal plantlets. SFPH can also serve as a general plant tissue culture nutrient, and can be used to create a complete medium for plant tissues that are otherwise difficult to grow in vitro.

Soluble fish protein hydrolysate (SFPH) is made from the solid waste left behind after fish processing. The world annual fish catch has been estimated to be approximately 71 million tons, only about 25 tons of which is used for human food. About 20 million tons is caught specifically to be made into fish meal. Of the remaining 26 million tons of "waste," about half is recovered for fish meal, while the rest is made up of bones and offal (Mackie, 1982, *Process Biochem.*, 17:26–31). This solid waste is high in protein, but to date has not been used effectively as a food supplement because it spoils quickly, which causes the fish waste to develop odors and flavors which persist through further processing, and the fats must be stabilized to prevent oxidation, which imparts a rancid odor. This is especially a problem in fatty fish, such as mackerel, which may contain up to 356% fat.

Use of Fishery By-Products to Increase the Rate of Somatic Embryogenesis

Many plants with horticultural value are currently propagated via tissue culture for the nursery industry. In 1990, it was estimated that as many as 1000 species of plants could be propagated by tissue culture at that time, and that up to 300 commercial laboratories were producing 20 million plants worldwide (Murashige, 1990, *Handbook of Plant Cell Culture*, Vol. 5, McGraw Hill, New York, pg. 5). Use of such methods may be expensive in some cases, but the laboratory costs can be offset by the advantages of producing a large number of certifiably identical, virus-free plants in a short time and in a small space. Such benefits are especially profitable in the production of patented plant varieties, fruit trees and bushes, and ornamental plants. Blackberries, raspberries, begonias, orchids, and others are amenable to this type of cultivation. A single shoot apex of *Vitis vinifera*, for instance, can be cultured into 8,000 plants in three to four months (Endress, 1994, *Plant Cell Biotechnology*, Springer-Verlag, Berlin, pg. 116).

Fishery by-products, e.g., SFPH, are added to plant tissue culture media in an amount that stimulates somatic embryogenesis and plant micropropagation, which is determined by comparing the number of embryos successfully generated on the previously-used culture medium with and without addition of the fishery by-products. Exact amounts will vary with the nutritional needs of the plant species or tissue being cultured, but a useful range is 50 milligrams to 5000 milligrams of SFPH per liter of culture media. More than 5000 milligrams was found to inhibit growth of the plants tested. A more appropriate range for some plants is 500 to 2000 milligrams per liter, however, the inventors have found 1000 milligrams of SFPH per liter of culture medium to be optimal for the plants grown in their laboratory.

To use SFPH to increase the rate of somatic embryogenesis, the hydrolysate is added to the culture medium immediately before pH adjustment, to ensure that the final pH of the medium is not altered by its addition. Solidifying agents, if they are to be used, are also added at this time, and the culture medium is autoclaved. After autoclaving, the medium is allowed to cool. Growth regulators and any other heat-labile ingredients that are to be used should be added as is normally done in the art, e.g., they should be filter-sterilized and added after the autoclaved medium has cooled, but before the solidifying agent has hardened. These heat-labile ingredients are mixed into the medium by gentle swirling, or some other commonly-used technique. If a solidifying agent was added, the medium is poured into petri dishes, test tubes, or other containers, and allowed to harden. If no solidifying agent is added, then the medium can be used as soon as it has cooled completely. Explants or other plant tissues are transferred to the medium, and incubated under the usual light, humidity, and temperature regimes in general use for that species.

Use of Fishery By-Products to Decrease Vitrification of Cultured Plant Tissues

Vitrification is believed to be due to extended exposure of plant tissues to air with a high relative humidity. The commonly accepted practice to reduce vitrification is to increase the concentration of a solidifying agent in the medium, so that the relative humidity is reduced within the culture vessel. Unfortunately, this also significantly reduces the rate of successful micropropagation in some species, possibly due to a buildup of impurities in the solidifying agent (Debergh et al., 1981, *Physiol. Plant.*, 53:181–187). Another way to reduce the relative humidity is to incubate the cultures at a lower temperature, but this is not feasible for plants with a limited viable temperature range or that exhibit a tendency to vitrify even at low relative humidities. In addition, it is difficult to consistently maintain a particular humidity level in this fashion because even small temperature variations, such as those found in normal incubation systems, can cause changes in the vapor pressure within the culture container. In situations where tissues vitrify while maintained in liquid culture, lowering the relative humidity of the air within the culture vessel is unlikely to have any effect, because the tissues are still kept in full contact with the liquid medium.

The amount of fishery by-products, e.g., SFPH, that is appropriate for controlling vitrification will vary with the species being treated. The appropriate range for preventing vitrification is similar to that used for enhancing somatic embryogenesis, e.g., the useful range is 50 milligrams to 5000 milligrams of SFPH per liter of culture media, with 500 to 2000 milligrams yielding better results with some plant tissues, while the inventors found that 750 to 1500 milligrams SFPH per liter was most appropriate for the species of plants studied in their laboratory. Addition of the SFPH to the medium is also the same as for induction of embryogenesis, e.g., the SFPH is added before pH adjustment and sterilization, so as to avoid altering the pH of the medium required by the plant tissues. Growth regulators appropriate for the cultured tissues are added after the medium has cooled, and explanted tissues are maintained on this media in the manner usual for that species.

Use of Fishery By-Products to Enhance Acclimation of Regenerated Plantlets

Plants grown under conventional conditions form a cuticle, a waxy outer layer that prevents evaporative water loss. Due to the high relative humidity inside culture containers, plants grown in tissue culture do not fully develop this protective layer, and may die of dehydration if suddenly placed in a growth chamber or greenhouse. Plants regenerated in tissue culture must be acclimated to prepare them for growth in a normal environment.

The most common method to accomplish this is to transplant the plantlets to sterile soil in closed containers, and then to reduce the relative humidity by gradual opening of the culture containers over several weeks. A series of lids that allow successively greater amounts of exchange with outside air can also be used.

The number of plantlets lost during this stressful process can be reduced by inclusion of fishery by-products such as SFPH in the culture medium during regeneration. A suitable amount is 750 to 1500 milligrams of SFPH per liter of culture medium, although 500 to 2000 milligrams per liter, or even 50 milligrams to 5000 milligrams per liter are useful ranges for different plant species. The method of formulating a culture medium containing SFPH is the same as that described for somatic embryogenesis or control of vitrification, e.g., inclusion of an amount of SFPH appropriate for the species of interest, added before pH adjustment and sterilization of the medium.

To use this medium to aid acclimation, embryos are transferred to this medium during regeneration into whole plants, or better still, the embryogenic tissue is also cultured on this medium during embryo induction. When the plantlets have reached an appropriate size and developmental stage, they are transplanted into sterile soil in pots. They should be covered with clear plastic for a few days to allow the cuticle to develop under reduced humidity, but after this period, the covering can be removed entirely, saving several weeks that would normally be required for cuticle development in untreated plants. After an additional two weeks of growth in the incubator or growth chamber, the plants are moved to greenhouse conditions. The acclimation period will vary depending on the plant species being treated, but the inventors have found that inclusion of SFPH in the culture medium generally reduces the acclimation period by approximately 50%.

Use of Fishery By-Products to Formulate a Complete Medium for Plant Tissue Culture Apart from the economic benefits of the mass propagation of valuable plants described above, plant tissue culture has another major use, that is, the production of virus-free plants. The plant vessels through which viral particles migrate terminate below the cells of a plant's growing shoot tip, effectively creating a barrier against the viral infection of these rapidly-dividing tissues. Culturing the cells of the vegetative meristem allows for creation and maintenance of certifiably virus-free stocks. This not only allows mass propagation of healthy plants, but more importantly, allows the shipping of plants and plant parts to other geographic regions. Because of the danger of spreading diseases to uninfected places, most plants and plant materials are not allowed to be shipped to other countries, or even other regions of the U.S., unless they are certified disease free. The ability to create virus-free strains therefore increases the potential market for these plants.

Unfortunately, there are still many plants that do not respond well to in vitro culture. The exact nutritional requirements of many important plant species have been investigated and are well understood, but the requirements of many more species remain unknown. The difficulty is that the chemical composition of the "ideal" medium can vary greatly not only between species, but between cultivars within a specie, and even from tissue to tissue. The media composition can also dictate the developmental pathways that the culture will take. For example, on one particular medium, one species of plant may grow quite well, while a closely-related species or cultivar may require adjustments to the medium. A particular tissue may produce small clonal plantlets on one medium, while another tissue taken from the same individual plant will produce only an undifferentiated mass of cells in that same petri dish. For this reason, cultures are often maintained on one type of media, and then transferred to others to initiate the development of roots, shoots, leaves, or whole plants.

When searching for the correct medium for a new plant or tissue, most practitioners of tissue culture begin their search with a medium that is already in common use. Some of the more commonly used media are White's (White, 1943, *A Handbook of Plant Tissue Culture*, Ronald Press Co., New York), Murashige and Skoog, or MS (Murashige & Skoog, 1962, *Physiol. Plant.*, 15:473–497), Schenk and Hildebrandt, or SH (Schenk & Hildebrandt, 1972, *Can. J. Bot.*, 50:199–204), and Gamborg's B5 medium (Gamborg et al., 1968, *Exp. Cell Res.*, 50:151–158). The choice between these media can usually be aided by examining the behavior of related plants that are already successfully cultured, if any. Once a basal medium is chosen, it must be refined by systematically varying its components. This can be a very laborious process. For example, testing the optimal ratio between two ingredients at five different concentrations results in 25 separate test treatments.

Because of the potentially vast number of parameters that need to be tested, many tissue culture practitioners begin their search for a new medium with "highly enriched" or "complete" media. These contain extracts of biological origin. They are generally less preferred, especially in industrial settings, than "regular" or "synthetic" media (which contain only well-defined chemical ingredients) because of the potential variation that can occur from batch to batch. Highly enriched media, however, are especially advantageous in cases where all other attempts at culture have failed, and the inclusion of a complex (although undefined) array of nutrients can allow the successful culture of a tissue for the amount of time required to more clearly research and understand the plant's in vitro nutritional requirements.

Highly enriched media generally contain plant juices and extracts. Coconut milk is the most common, or juices from the plant for which the media is being defined. The inventors have found that fishery by-products such as SFPH, an extract of non-plant origin, can be used as an ingredient in the formulation of complex media for use in culturing plant species and tissues previously not amenable to culture.

An advantage of the invention is that SFPH is high in amino acids generally. Supplementing culture media with only one or two purified amino acids may impair some metabolic pathways in the cultured tissues, e.g., extra threonine, glycine, or valine are known to cause diminished ammonia assimilation by inactivating glutamate synthase (Endress, 1994, *Plant Cell Biotechnology*, Springer-Verlag, Berlin, pgs. 33–34). Use of SFPH as an addendum to the medium avoids this problem.

Another advantage of the invention is that SFPH is an excellent source of nitrogen. Murashige & Skoog medium, which is very commonly used in the art, sometimes causes ammonium toxicity in some species (Endress, 1994, *Plant Cell Biotechnology*, Springer-Verlag, Berlin, pg. 38). In such cases, the $NH_4NO_3$ must be reduced substantially or entirely, and replaced with other sources of nitrogen. SFPH can be used as the nitrogen source in these situations, making up for this deficiency in this commonly-used medium.

Certain amino acids, particularly proline, have been found to enhance somatic embryogenesis on their own (Armstrong & Green, 1985, *Planta*, 164:207–214; Stuart & Strickland, 1984, *Plant Sci. Lett.*, 34:165–174). The inventors have found that the addition of SFPH to the culture medium can produce results similar to those achieved by proline alone (see Example 1 below), and embryogenesis can be enhanced further still by inclusion of both proline and SFPH in the culture medium.

EXAMPLES

Example 1

Use of Fishery By-products in Promoting Somatic Embryogenesis

Explants were taken from roots of anise (*Pimpinella anisum*) lines A-1 and A-8. Each line was started from a single heterozygous seed, and these two were chosen because A-8 typically responds favorably to experimental treatments and endogenously produces higher levels of chlorophyll and lignin, while A-1 tends to exhibit a poorer embryogenic response in culture. Callus from the root explants was induced and maintained on Schenk and Hildebrandt (SH) hormone-free medium (Schenk & Hildebrandt, 1972, *Can. J. Bot* ., 50:199–204), and cultured at 25° C. under fluorescent light with an intensity of 40 $\mu Em^{-2}s^{-1}$, on a cycle of 16 hours of light per day.

To induce somatic embryos, the root callus was transferred to standard Murashige and Skoog (MS) medium (Murashige & Skoog, 1962, *Physiol. Plant.*, 15:473–497) with 1 milligram per liter 2,4-D (2,4-dichlorophenoxyacetic acid) and 3%. sucrose added. The following experimental supplements were also added: none (control), cod hydrolysate (1000 milligrams per liter), herring hydrolysate (1000 milligrams per liter), 5 mM proline, 5 mM proline plus 1000 milligrams per liter cod hydrolysate, or 5 mM proline plus 1000 milligrams per liter herring hydrolysate. Proline is known to have a stimulatory effect on somatic embryo formation from appropriate plant tissue explants (Armstrong & Green, 1985, *Planta*, 164:207–214; Stuart & Strickland, 1984, *Plant Sci. Letters*, 34:165–174,175–181). Both fish hydrolysates were obtained from Ocean Crest, Inc., Gloucester, Mass. After adjusting the pH of the medium to 6.8 with either 1N NaOH or 1N HCl, 0.275% Gelrite was added as a solidifying agent. The medium was autoclaved under standard conditions, and dispensed into petri dishes. Pieces of the root callus were transferred to this medium and maintained for 20 to 25 days under the same lighting conditions as described above.

After 50 days, the explants were examined under a stereomicroscope, and the number of embryos that had formed per explant was counted. Each treatment was repeated four times, with eight explants per plate.

The results are shown in Table 1, which shows the influence of proline and fish protein hydrolysates on somatic embryogenesis in anise. Means within a column that are followed by the same letters are not significantly different at the 5% level by Duncan's multiple range test. Clonal line A-8 exhibited a much greater overall response to all treatments than did A-1, but the pattern of that response was similar in both lines. As expected, A-1 responded to the treatments in a manner similar to that of line A-8, but to a much lesser extent (Table 1).

TABLE 1

| Treatment | % of Total Explants Forming Embryos | | Average Number of Embryos Per Responding Explant | | Total Number of Embryos per 32 Explants | |
| --- | --- | --- | --- | --- | --- | --- |
| | A-1 | A-8 | A-1 | A-8 | A-1 | A-8 |
| Control | 9 | 56 | 2 a | 9 a | 6 | 162 |
| Proline (5.0 mM) | 9 | 94 | 2 a | 14 b | 6 | 420 |
| Cod (1000 mg/l) | 6 | 72 | 7 b | 18 b | 14 | 414 |
| Herring (1000 mg/l) | 0 | 19 | 0 a | 16 b | 0 | 96 |
| Proline (5.0 mM) + Cod (1000 mg/l) | 16 | 63 | 17 c | 72 c | 85 | 1440 |
| Proline (5.0 mM) + Herring (1000 mg/l) | 6 | 35 | 6 b | 82 c | 12 | 902 |

In single treatments, i.e., cod or herring or proline alone, the cod hydrolysate had a much stronger effect than herring hydrolysate in both lines. This was true of the total number of explants that formed embryos, the average number of embryos produced by those explants, and the total number of explants produced overall. Interestingly, although proline showed the greatest increase in the number of explants that actually formed embryos, the number of explants produced per explant was stimulated more strongly by the fish hydrolysates. In fact, if the results are examined in terms of the total number of somatic embryos produced among the 32 explants in each treatment (Table 1, last 2 columns), the cod hydrolysate stimulated formation of nearly as many embryos as the proline treatment in the A-8 line, and actually performed better than the proline treatment in the A-1 line.

Combining the treatments, i.e., fishery by-products plus proline, produced even greater increases in the regeneration rate. For line A-1, the cod hydrolysate plus proline treatment caused the greatest increase in the percentage of explants that formed embryos, in the average number of embryos per responding explant, and in the total number of embryos formed across 32 explants.

For line A-8, the situation was more complex. Proline alone resulted in the largest percentage of explants that formed embryos, but the average number of embryos formed on those responding explants was not increased much above controls. Cod hydrolysate caused nearly as many explants to produce embryos, and each explant produced more embryos than under the proline treatment. The net result was that the total number of embryos produced was nearly identical for the proline and the cod treatments.

The greatest increase occurred under the combined fish hydrolysate plus proline treatment. More than twice as many embryos were produced with this treatment as with any other (Table 1, last column). In a commercial nursery setting, addition of both fish hydrolysate and proline to the regeneration medium would be the most efficient method of producing the greatest number of propagules.

Addition of amino acids to culture media has been used in the past in an attempt to improve the rate of embryogenesis. Results have been mixed, however. Certain amino acids, particularly proline, have been found to enhance somatic embryogenesis on their own in some species (Armstrong & Green, 1985, *Planta*, 164:207–214; Stuart & Strickland, 1984, *Plant Sci. Lett.*, 34:165–174). Generally, however, the addition of individual amino acids inhibits growth (Endress, 1994, *Plant Cell Biotechnology*, Springer-Verlag, Berlin, pg. 116; Trigiano & Conger, 1987, *J. Plant Physiol.*, 130:49–55). Proline generally enhances somatic embryogenesis, but can be inhibitory at high levels (Shetty et al., 1992, *Plant Tissue Culture Letters*, 9:104–108; Shetty & Asano, 1991, *Plant Science*, 79:259–263; Armstrong & Green, 1985, *Planta*, 164:207–214). The inventors have found that additions of SFPH greater than 5000 milligrams per liter inhibited the growth of the plant tissues tested. Therefore, the addition of such large concentrations of the fish hydrolysates, especially the herring, may raise the proline concentration to inhibitory levels.

Example 2
Improved Control of Vitrification in Oregano by Inclusion of Fish Protein Hydrolysate in the Medium Tissue Culture and Media Shoot cultures were initiated from previously isolated oregano clonal line 0-1 following the procedure outlined by Shetty et al., 1995, J. Plant Physiol. 147:447–451. Briefly, oregano seeds were germinated and allowed to grow for 30 days. Individual shoot apices were then excised, and transferred to petri plates containing MS medium with 4.44 mM benzylaminopurine (BAP), and 3% sucrose, at pH 5.8. Phytagel (Sigma Chemical-Gellan gum) at a concentration of 0.3% was used as the solidifying agent. Seven shoot apices were placed on each of four petri plate and were incubated at 24° C., with a 16 hour light cycle at an intensity of 40 $\mu Em^{-2}s^{-1}$. After 30 days the shoot apex explants regenerated more apices through axillary shoot proliferation. These new shoot apices were then subcultured for an additional 30 days to study the effects of different protein hydrolysates on vitrification in cultured tissues. The entire experiment was done twice.

Determination of Optimal Hydrolysate Concentration

The prevention of vitrification in the proliferating shoots was compared among treatments of 0, 500, 1000, 2000, 3000, 4000, and 5000 milligrams per liter of the following protein hydrolysates: atlantic cod hydrolysate, herring hydrolysate (both supplied by Ocean Crest, Inc. Gloucester, Mass), yeast extract (Sigma Chemicals, St. Louis, Mo.), bacto-peptone (Difco Laboratory, Detroit, Mich.), and casein enzymatic hydrolysate (Sigma Chemicals, St. Louis, Mo.). The hydrolysates in dry powder form were added to the standard BAP-containing MS medium described above. The media were sterilized by autoclaving under standard conditions. After 30 days of culture on this media, the shoots were examined by stereomicroscope. Treated shoots were compared visually to controls to determine the percentage of shoots in each treatment that exhibited lower levels of chlorophyll, and displayed characteristics of vitrification, e.g., long, spindly stems, curled leaves, and brittle and transluscent tissues. Based upon these observations (data not shown), it was decided that 1000 milligrams per liter was an appropriate level for further testing with fish hydrolysates, casein hydrolysate, and bacto-peptone. Yeast extract was also tested, but was found to cause partial inhibition of growth at 500 milligrams per liter, and complete inhibition at levels of 1000 milligrams or more.

Each protein hydrolysate was added at the selected concentration to the standard BAP-containing medium. Oregano shoots were transferred to these media and incubated for 30 days. Each treatment in this study had 28 explants per petri plate, and the entire experiment was performed twice, for a total of 56 explants. After 30 days of incubation, the degree of vitrification was again determined by stereomicroscopic observations, and also by total phenolics and chlorophyll content. The visual data were expressed as percent of cultures that were vitrified.

Total Phenolics

Total phenolics were determined according to previous methods (Chandler and Dodds, 1983, *Plant Cell Rep.*, 2:105–108), modified for oregano (Shetty et al., 1995, *J. Plant Physiol.*, 147:447–451). Approximately 50 milligrams (fresh mass) of shoot tips were placed in 2.5 milliliters of 95% ethanol and held at 0° C. for 48 hours. Each sample was homogenized and centrifuged at 13,000×g for 5 minutes. One milliliter of the supernatant was transferred to a 16×100 millimeter test tube and 1 milliliter of 95% ethanol, 5 milliliters of distilled water, and 0.5 milliliter of 50% Folin-Ciacalteu reagent (Sigma Chemicals, St. Louis, Mo.) were added to each test tube. After 5 minutes, 1 milliliter of 5% $Na_2CO_3$ was added to each sample, then mixed and placed in darkness for one hour. The absorbance was read at 725 nanometers with 95% ethanol as a blank. Standard curves were established for each experiment using various concentrations of gallic acid (Fisher Scientific) in 95% ethanol. The results were represented as milligrams phenolic compounds per gram tissue.

Total Chlorophyll

Total chlorophyll was measured by spectrophotometric methods (Hipkins and Baker, 1986, In: Hipkins, et al., eds. *Spectroscopy*, IRL Press, Oxford, Wash., pgs. 51–100), modified for oregano (Shetty et al., 1995, *J. Plant Physiol.*, 147:447–451). Approximately 50 milligrams (fresh mass) of oregano explants were placed in 5-milliliter vials and 3 milliliters of 100% methanol was added to each vial. The vials were incubated at room temperature for 2 hours in darkness. The methanol fraction in each sample was decanted, and the absorbance was measured at 650 and 665 nanometers. Total chlorophyll ($C_T$) was expressed as micrograms per milliliter of methanol using the formula:

$$C_T = 25.8 \times A_{650} + 4.0 \times A_{665},$$

where $A_{650}$ and $A_{665}$ are the absorbance at 650 and 665 nanometers respectively. The total chlorophyll was then converted to micrograms of chlorophyll per gram of tissue.

Water Content 500 milligrams (fresh mass) of shoot explants were placed in preweighed aluminum pans and allowed to dry for 24 hours at 55° C. Pans were weighed at 24 hours and 36 hours to confirm weight constancy. Water content was estimated and expressed on a 100 milligram wet mass basis.

Results

Results are shown in Tables 2 and 3. Table 2 shows the degree of vitrification in response to various protein hydrolysates. The results are from two separate experiments with 28 shoot explants per treatment per experiment. More than half of the control shoots (54%) became vitrified over 30 days of culture. Inclusion of bacto-peptone in the medium reduced this rate to 29% vitrification. The fish hydrolysates exhibited nearly the same rate, with the cod and the herring hydrolysate resulting in 29% and 25% hyperhydricity, respectively.

TABLE 2

| Treatment | Total Shoots | % Vitrification | % Normal Plants With Higher Chlorophyll |
|---|---|---|---|
| Control | 56 | 54% | 48% |
| Yeast extract (200 mg/l) | 56 | 66% | 32% |
| Bacto-peptone (1000 mg/l) | 56 | 29% | 71% |
| Casein hydrolysate (1000 mg/l) | 56 | 45% | 54% |
| Cod hydrolysate (1000 mg/l) | 56 | 29% | 71% |
| Herring hydrolysate (1000 mg/l) | 56 | 25% | 75% |

The effects of the different treatments on the total water, phenolics, and chlorophyll content are shown in Table 3. Table 3 shows chlorophyll, phenolics, and water content of shoots following 30 days of growth in medium supplemented with various protein hydrolysates. Means in a column that are followed by the same letters are not significantly different from each other at the 5% level by Duncan's multiple range test. Means were obtained from two separate experiments in which each treatment was done in triplicate.

Water content was significantly lower for the yeast extract and bacto-peptone treatments, while the casein, cod, and herring hydrolysates were similar to the control. The difference between the two groups was small, however, and certainly nowhere near the differences between vitrified and unvitrified tissue that have been reported in the literature. For example, Kevers et al. (1984, *Physiol. Plant.*, 61:69–74), reported rates ranging anywhere from 0% to 43% in the reduction in dry weight between vitrified and unvitrified tissues within a given species.

In addition, water content can vary depending on whether the tissues are fully or partially vitrified, making chlorophyll content a more reliable indicator of vitrification.

TABLE 3

| Treatment | Water mg/100 mg tissue | Total Chlorophyll ($\mu$g tissue) | Phenolics (mg/g tissue) |
|---|---|---|---|
| Control | 90.6 a | 474 b | 2.1 a |
| Yeast extract (200 mg/1) | 86.6 b | 198 a | 6.2 c |
| Bacto-peptone (1000 mg/l) | 87.6 b | 428 b | 6.6 c |
| Casein hydrolysate (1000 mg/1) | 90.8 a | 440 b | 3.8 b |
| Cod hydrolysate (1000 mg/l) | 89.7 a | 708 c | 3.1 ab |
| Herring hydrolysate (1000 mg/1) | 89.8 a | 1087 d | 3.5 b |

Total content of phenolics (a common indicator of stress in plants) exhibited behavior similar to that of water content, with the casein, cod, and herring containing slightly more total phenolics than the control.

Reduction in the total chlorophyll content is a useful indicator of vitrification (Böttcher et al., 1988, *Physiol. Plant.*, 72:560–564), and was much higher in the shoots grown on medium containing the fish hydrolysates, as shown in Table 3. Shoots grown with yeast extract had much lower chlorophyll levels than the controls, while the bactopeptone and casein hydrolysate treatments were roughly equivalent to the controls. The shoots grown on medium containing cod hydrolysate, however, had much more chlorophyll than the controls, while the herring hydrolysate-treated shoots had more than double the chlorophyll of the controls. The shoots themselves were also far more vigorous, healthy-looking, and greener, with greater rigidity of the tissues. The intermodes were about 50–75% shorter, and the shoots themselves were more compact, and about 30% smaller. The control shoots were long and spindly, and the leaves were transluscent and yellowed.

Example 3

Improved Acclimation of Oregano by Inclusion of Fish Protein Hydrolysate in the Medium Materials and methods were exactly as described for Example 2, above, except that instead of culturing the newly-generated shoot apices for an additional 30 days (see the end of the section "Tissue Culture and Media," Example 2, above), they were moved to hormone-free, half-strength MS medium, and regenerated into plantlets to study the effects of bacto-peptone and herring hydrolysate on successful regeneration, acclimation, and overall survival.

Acclimation Studies

Oregano shoot apices were regenerated into whole plants on media supplemented with either bacto-peptone or herring hydrolysate. They were then transferred to soil in pots to test acclimation and survival. Acclimation was accomplished by placing the pots in a black tray under constant light at room temperature. The pots were covered with a transparent plastic top for the first 10 days, at which point the total number of oregano shoots that survived was counted. The plastic top was then removed. The oregano shoots that survived after 48 hours following this sudden exposure were then counted. The surviving plants were than allowed to grow for 30 days (unacclimated) and plant vigor was estimated visually. The experiment was repeated three times, and twelve shoots were tested in each experiment.

Results

The results are shown in Table 4. Table 4 shows the effect of different protein hydrolysates on normal plant development and acclimation in soil. Fewer of the bacto-peptone-treated shoots than the control survived the 10-day acclimation period under the plastic wrap. Fewer still survived the sudden exposure to ambient air and humidity, and those that did survive showed little or no growth. The shoots grown on media that included herring hydrolysate, however, performed better than controls. The internodes were 50–75% shorter than the vitrified controls, and the shoots were more compact, and about 30% smaller overall. The tissues themselves were darker green, and more rigid than controls, which had thin spindly stems and yellowish, transluscent leaves. Survival rates through both the acclimation period and the sudden exposure to ambient conditions were 61%, 25%, and 53% of the total for the herrring hydrolysate, the bacto-peptone, and the controls, respectively. Of the plants that survived through the acclimation process, 50 to 60% of the fish hydrolysate-treated plants displayed vigorous growth over the next 30 days. The controls exhibited low growth, and uniformly lacked vigor. The plants treated with bacto-peptone failed to grow any larger.

TABLE 4

| Treatment | Total Shoots | % Survival with 10 days acclimation | % Survival after 48 hours of exposure following acclimation for 10 days | Plant growth after 30 days of exposure following acclimation for 10 days* |
| --- | --- | --- | --- | --- |
| Control | 36 | 72% | 53% | + |
| Bacto-peptone (1000 mg/l) | 36 | 42% | 25% | − |
| Herring hydrolysate (1000 mg/l) | 36 | 81% | 61% | +++ |

* − no growth;
+ low vigor/light green;
++ medium vigor;
+++ high vigor/dark green A previous study (Sato et al., 1993, *Plant Cell Rep.*, 12:370–374) maintained that bacto-peptone reverses vitrification and enhances acclimation, but that was not found to be the case here. In the present study, most of the oregano shoots on bacto-peptone-supplemented medium did not survive the acclimation and exposure process (Table 3) even after the shoots had regenerated normally during the 30 days of in vitro culture. The herring hydrolysate-treated shoots fared better at each point in the acclimation process. About 61% of the shoots on the medium supplemented with herring hydrolysate survived the acclimation and exposure process and all the recovered plants had mechanical rigidity of the branches and were free of vitrification. The plants treated with herring hydrolysate were dark green, i5 vigorous, and had intermodes approximately half the length of the control shoots. The shoots treated with the herring hydrolysate were more compact overall.

Therefore, although inclusion of bacto-peptone in the medium inhibited the vitrification of shoots while in culture (Example 2, above), it also prevented the later acclimation of shoots to the outside environment.

OTHER EMBODIMENTS

It is to be understood that while the invention has been described in conjunction with the detailed description thereof, that the foregoing description is intended to illustrate and not limit the scope of the invention, which is defined by the scope of the appended claims.

Other aspects, advantages, and modifications are within the scope of the following claims.

What is claimed is:

1. A composition for use in plant tissue culture, the composition comprising
   (a) a plant tissue culture medium,
   (b) a fishery by-product, wherein the plant tissue culture medium and fishery by-product are mixed in proportions to form a homogeneous mixture, wherein the fishery by-product is selected from the group consisting of fish protein hydrolysate, unhydrolysed fish waste, fish meal, fish gurry, and fish offal.

2. A plant tissue culture composition of claim 1, wherein the plant tissue culture medium is selected from the group consisting of Murashige & Skoog medium, Schenk & Hildebrandt medium, White's medium, and Gamborg's B5 medium.

3. A plant tissue culture composition of claim 1, wherein the composition is a solid.

4. A plant tissue culture composition of claim 1, wherein the composition is a liquid.

5. A plant tissue culture composition of claim 1, wherein the composition further comprises a compound to adjust the pH to a level suitable to support the culture of plant tissue.

6. A plant tissue culture composition of claim 1, wherein the composition further comprises one or more plant growth regulators.

7. A plant tissue culture composition of claim 1, further comprising an amino acid or amino acid analog.

8. A plant tissue culture composition of claim 7, wherein the amino acid is proline.

9. A plant tissue culture composition of claim 1, wherein the fishery by-product is added in an amount adequate to increase production of somatic embryos by cultured plant tissues relative to use of the plant tissue culture medium without the fishery by-product.

10. A plant tissue culture composition of claim 1, wherein the fishery by-product is added in an amount adequate to inhibit vitrification of cultured plant tissues relative to use of the plant tissue culture medium without the fishery by-product.

11. A plant tissue culture composition of claim 1, wherein the fishery by-product is added in an amount adequate to improve acclimation of cultured plant tissues relative to use of the plant tissue culture medium without the added fishery by-product.

12. A method of using a fishery by-product composition in plant tissue culture, the method comprising
   (a) obtaining a plant tissue culture medium,
   (b) adding a fishery by-product to form a composition, wherein said fishery by-product is selected from the group consisting of fish protein hydrolysate, unhydrolysed fish waste, fish meal, fish gurry, and fish offal,
   (c) mixing the composition to form a homogeneous mixture, and
   (d) using the composition as a substrate for culturing plant tissues, wherein said composition enhances the growth of said plant tissues.

13. A method of claim 12, wherein the plant tissue culture medium is selected from the group consisting of Murashige & Skoog medium, Schenk & Hildebrandt medium, White's medium, and Gamborg's B5 medium.

14. A method of claim 12, wherein the composition is a solid.

15. A method of claim 12, wherein the composition is a liquid.

16. A method of claim 12, wherein the pH of the plant tissue culture medium is adjusted to achieve a pH suitable to support the culture of plant tissue.

17. A method of claim 12, wherein the method further comprises the addition of one or more plant growth regulators.

18. A method of claim 12, wherein the method further comprises the addition of amino acids or amino acid analogs to the composition prior to mixing.

19. A method of claim 18, wherein the amino acids and amino acid analogs are selected from a group consisting of proline and proline analogs.

20. A method of claim 18, wherein the amino acid is proline.

21. A method of claim 12, wherein the method is used to increase production of somatic embryos by cultured plant tissues relative to use of the plant tissue culture medium without the fishery by-product.

22. A method of claim 12, wherein the method is used in to increase plant growth relative to use of the plant tissue culture medium without the fishery by-product.

23. A method of claim 12, wherein the method is used to inhibit vitrification of plant tissues relative to use of the plant tissue culture medium without the fishery by-product.

24. A method of claim 12, wherein the method is used to improve acclimation of cultured plant tissues relative to use of the plant tissue culture medium without the added fishery by-product.

* * * * *